US011103636B2

(12) United States Patent
Olivas et al.

(10) Patent No.: US 11,103,636 B2
(45) Date of Patent: Aug. 31, 2021

(54) NEEDLE INSERTION MECHANISM FOR DRUG DELIVERY DEVICE (71) Applicant: AMGEN INC., Thousand Oaks, CA (US)

(72) Inventors: Jerome Olivas, Thousand Oaks, CA (US); Justin Harris, Reseda, CA (US); Sudeshna Dutta Ray, Thousand Oaks, CA (US); David Coleman, Dublin (IE); Eoghan McManus, Dublin (IE)

(73) Assignee: AMGEN INC., Thousand Oaks, CA (US)

( * ) Notice: Subject to any disclaimer, the term of this patent is extended or adjusted under 35 U.S.C. 154(b) by 162 days.

(21) Appl. No.: 16/015,568

(22) Filed: Jun. 22, 2018

(65) Prior Publication Data
US 2019/0060562 A1 Feb. 28, 2019

Related U.S. Application Data (60) Provisional application No. 62/548,750, filed on Aug. 22, 2017.

(51) Int. Cl.
*A61M 5/142* (2006.01)
*A61M 5/158* (2006.01)
(Continued)

(52) U.S. Cl.
CPC .... *A61M 5/14244* (2013.01); *A61M 5/14248* (2013.01); *A61M 5/158* (2013.01);
(Continued)

(58) Field of Classification Search
CPC ......... A61M 2005/14252; A61M 2005/14284; A61M 2005/1585; A61M 2005/14272;
(Continued)

(56) References Cited

U.S. PATENT DOCUMENTS

2006/0200073 A1   9/2006  Radmer et al.
2010/0331824 A1  12/2010  Moberg et al.
(Continued)

FOREIGN PATENT DOCUMENTS

WO   WO-2016/130679 A2   8/2016
WO   WO-2017/139741 A1   8/2017

OTHER PUBLICATIONS

International Application No. PCT/US2018/047409, International Search Report and Written Opinion, dated Oct. 31, 2018.

*Primary Examiner* — Nathan R Price
*Assistant Examiner* — Tania Ismail
(74) *Attorney, Agent, or Firm* — Marshall, Gerstein & Borun LLP (57) ABSTRACT An insertion mechanism for a wearable drug delivery device includes a needle hub, a needle coupled to the needle hub, a flexible boot removably coupled to the needle hub, and a cannula coupled to the flexible boot. The needle hub, the needle, the flexible boot, and the cannula are movable between a first position and a second position. Upon moving the needle hub, the needle, the flexible boot, and the cannula from the first position to the second position, the cannula engages a floor member to restrict movement of the cannula and the flexible movement towards the first position.

25 Claims, 4 Drawing Sheets (51) Int. Cl.
*A61M 5/24* (2006.01)
*A61M 5/20* (2006.01)

(52) U.S. Cl.
CPC ................ *A61M 5/24* (2013.01); *A61M 5/20* (2013.01); *A61M 2005/14252* (2013.01); *A61M 2005/14272* (2013.01); *A61M 2005/14284* (2013.01); *A61M 2005/1585* (2013.01)

(58) Field of Classification Search
CPC .......... A61M 5/14244; A61M 5/14248; A61M 5/158; A61M 5/24; A61M 5/20
See application file for complete search history.

(56) References Cited

U.S. PATENT DOCUMENTS

| | | | |
|---|---|---|---|
| 2014/0088509 A1* | 3/2014 | Sonderegger | A61M 5/3287 604/157 |
| 2015/0190588 A1* | 7/2015 | Hanson | A61M 5/14248 604/123 |

* cited by examiner

NEEDLE INSERTION MECHANISM FOR DRUG DELIVERY DEVICE

CROSS-REFERENCE TO RELATED APPLICATIONS

The priority benefit of U.S. Provisional Patent Application No. 62/548,750, filed Aug. 22, 2017, is claimed and the entire contents thereof are incorporated by reference herein.

FIELD OF THE DISCLOSURE

The present disclosure generally relates to drug delivery devices and, more particularly, enabling a sterile fluid flow path between a drug container assembled within a drug delivery device and a patient.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient. Some drug delivery devices, such as on-body injectors, may be temporarily attached to a patient to deliver a drug via an injection needle or some other means over an extended period of time. The drug delivery device may be attached to the tissue of the patient's abdomen, thigh, arm, or some other portion of the patient's body.

In some cases, the drug delivery device may be worn by the patient for several minutes or hours while the drug is injected. As an example, viscous drugs, including some biologics, can have long injection times due to the force needed to expel them from the drug delivery device. Some drug delivery devices are configured to be attached to the patient at a doctor's office, and then later deliver the drug to the patient when the patient returns to their home. Accordingly, a rigid injection member may be left inside the patient for a substantial amount of time, which can result in patient discomfort or unease.

To address this issue, some drug delivery devices incorporate a cannula made of a flexible material for delivering the drug to the patient. Such a cannula can bend to adjust to the patient's body movements and therefore may be more comfortable than a rigid needle. However, due to its flexibility, the cannula may have difficulty penetrating the patient's skin during insertion. Accordingly, an introducer needle or trocar is typically used to initially penetrate the skin and create a passageway for the cannula. The needle may be subsequently retracted, leaving the cannula partially inside the patient's body.

The insertion and/or retraction movements of the trocar and/or cannula may be accomplished by incorporating an insertion mechanism disposed within the drug delivery device. Such an insertion mechanism, however, may increase the overall size, complexity, and/or manufacturing costs associated with the drug delivery device by requiring a difficult manufacturing process that can require significant amounts of material. For example, current systems use a coiled tube as a fluid path between a drug container and an insertion mechanism. Upon actuation of the device, the coiled tube extends in order to move along with the insertion mechanism during the insertion process. Because of the length of the coiled tube, leftover drug product may remain in the fluid path after the drug delivery process is complete, and thus, excess product must be provided and ultimately discarded. Additionally, the coiling process can be both time consuming and costly.

SUMMARY

One aspect of the present disclosure provides an insertion mechanism for a wearable drug delivery device that includes a needle hub, a needle coupled to the needle hub, a flexible boot, a cannula, an urging member, and a floor member. The needle hub is movable between a first position and a second position. The flexible boot has a first end and a second end and defines an interior volume. The flexible boot is removably coupled to the needle hub and is movable therewith between the first position and the second position. The cannula is at least partially disposed within the interior volume of the flexible boot and includes a first end, a second end, a longitudinal length extending therebetween, and a hollow interior to accommodate the needle. The cannula further has a first cannula coupling mechanism located near the first end of the cannula and a second cannula coupling mechanism located between the first and second ends of the cannula. The first cannula coupling mechanism is coupled to the boot to be movable therewith between the first position and the second position. The urging member is in contact with the needle hub to urge the needle hub towards the first position. The floor member is positioned near the second end of the flexible boot and includes a floor coupling mechanism that extends into the interior volume of the flexible boot. Upon the needle hub occupying the second position, the second cannula coupling mechanism engages the floor coupling mechanism, thereby restricting movement of the cannula towards the first position.

In some examples, the first floor coupling mechanism includes a first angled tab having a first mating region. Further, the second cannula coupling mechanism may be in the form of a second angled tab protruding radially from the cannula and having a second mating region. Upon the second cannula coupling mechanism slidingly engaging the floor coupling mechanism, the first mating region of the first angled tab abuts the second mating region of the second angled tab.

In some forms, upon the needle hub being urged to the first position, the flexible boot disengages from the needle hub to remain at the second position. The flexible boot may be removably coupled to the needle hub via an interference fit.

In some approaches, a portion of the urging member abuts against the flexible boot to urge the flexible boot against the floor member. The urging member may be in the form of a coil spring having a grounded end that abuts against the flexible boot to form a seal.

In an example, the insertion mechanism further includes an insertion mechanism housing having a first end corresponding to the first position of the needle hub and a second end corresponding to the second position of the needle hub. The insertion mechanism housing defines an interior volume to accommodate the needle hub, the flexible boot, the cannula, and the urging member. The needle hub can include at least one tab. The insertion mechanism housing can include at least one channel extending between the first end and the second end thereof to accommodate and guide movement of the needle hub tab between the first position and the second position.

In some examples, the floor member includes a grooved restraint portion to accommodate a manufacturing restraint during assembly.

A second aspect of the present disclosure provides a wearable drug delivery device having a housing, a container disposed therein, an insertion mechanism having any number of the features of the previously described insertion mechanism, and a fluid pathway connector. The fluid pathway connector defines a sterile fluid flow path between the container and the insertion mechanism.

A third aspect of the present disclosure provides a method of manufacturing a needle injection mechanism for a wearable drug delivery device. A floor member is provided that has a contact surface and a floor coupling mechanism extending from the contact surface. A contact surface of a flexible boot is disposed against the contact surface of the floor member. The flexible boot defines an interior volume. An urging member is disposed against the flexible boot to retain the flexible boot between the urging member and the floor member. An insertion assembly is disposed within the interior volume of the flexible boot. A needle hub is coupled to the flexible boot and the insertion assembly. The floor member is disposed against a housing that defines an interior volume such the interior volume of the housing receives at least part of the flexible boot, the urging member, the insertion assembly, and the needle hub.

In some examples, disposing the insertion assembly in the interior volume of the flexible boot includes inserting a needle through a portion of the flexible boot such that a longitudinal length of the needle is within the interior volume of the flexible boot. In some examples, a cannula may be attached to the cannula prior to disposing the insertion assembly in the interior volume of the flexible boot. Disposing the urging member against the flexible boot may include disposing a grounded end of a coil spring against the flexible boot to form a seal. Coupling the needle hub to the flexible boot includes press fitting a portion of the flexible boot into an engagement region of the needle hub. Coupling the needle hub to the needle includes molding a needle elbow portion of the needle to the needle hub.

BRIEF DESCRIPTION OF THE DRAWINGS

The above needs are at least partially met through provision of the hydraulic-pneumatic pressurized chamber drug delivery system described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a needle insertion mechanism and methods of manufacturing the same. Generally, the needle insertion mechanism includes a needle that is inserted into a patient's subcutaneous tissue and is subsequently retracted. The needle insertion includes a cannula that is inserted into the patient's skin with the needle. Upon the needle insertion mechanism being activated (i.e., moving from a first position to a second position where the needle is inserted into the patient's skin), the cannula is configured to engage a floor member and remain in the second, fixed position. The cannula is coupled to a flexible boot member that moves along with the cannula to the second, fixed position, and assists in maintaining a sterile pathway for the liquid drug product to travel from the device into the patient.

Because the cannula itself engages the floor member, the number of components is reduced relative to known existing designs, thus lowering manufacturing time and costs while improving operating efficiency and reliability. Further, such a configuration allows for the insertion mechanism to be assembled in a simple top-down approach whereby the entire mechanism can be assembled in a stable, sterile environment, among other advantages. The disclosed needle insertion mechanism can be part of a larger drug delivery device such as a wearable on-body injector. One example of such a drug delivery device is therefore described with respect to FIG. 1.

Figure 1:
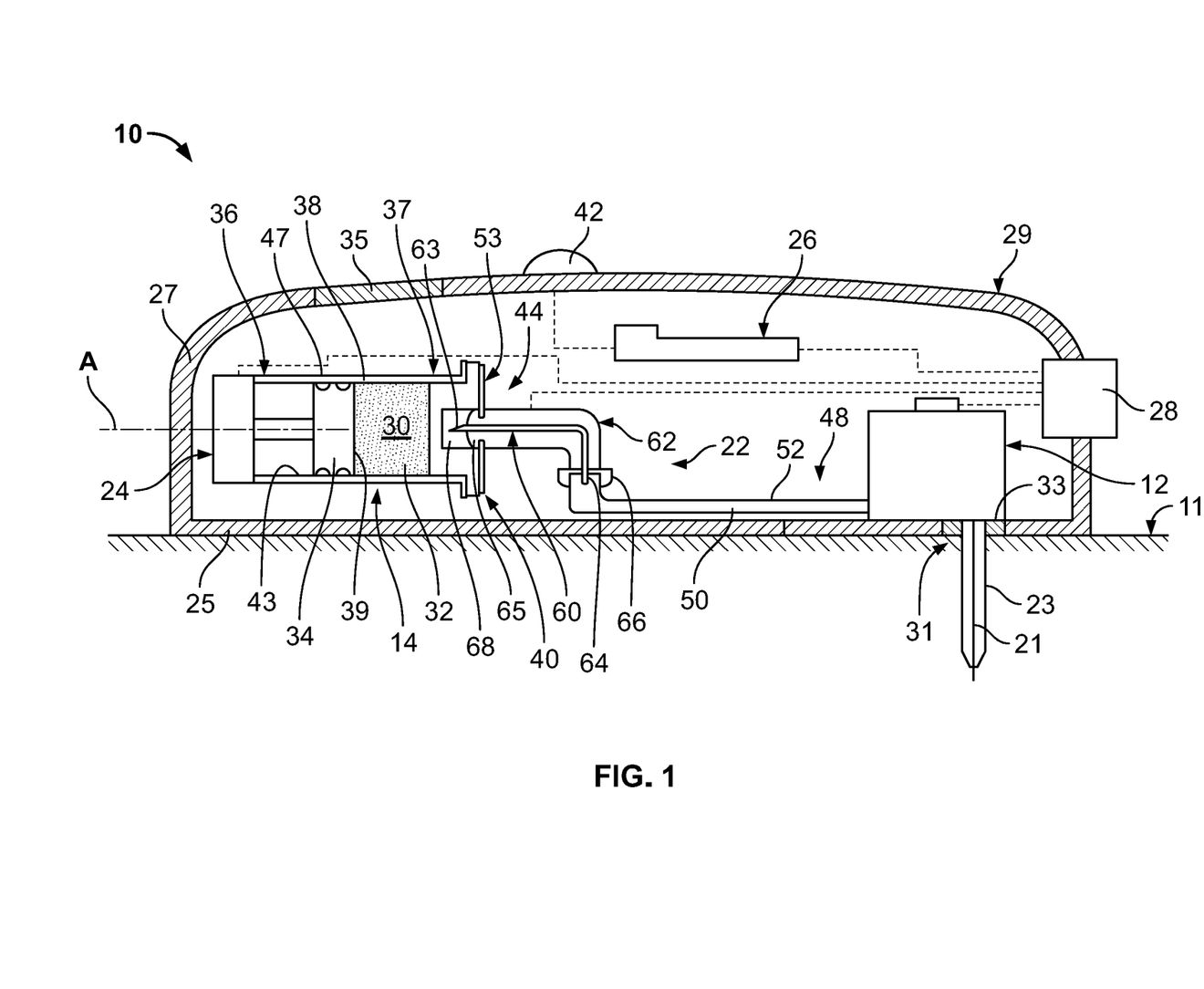
FIG. 1 illustrates a schematic cross-sectional view of an embodiment of a drug delivery device in accordance with various embodiments.

FIG. 1 is a schematic illustration of one embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). In other embodiments (not illustrated), the drug delivery device 10 may be configured as a pen-type injector, such as an autoinjector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container 14, or cause the container 14 to move towards the stationary fluid pathway assembly 22, and thereby cause a container access needle to penetrate through a seal member into a reservoir or interior volume of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a drug 32 contained therein. The one or more visual indicators 42 may be used to communicate information to the user about the operational state of the drug delivery device 10 and/or the condition of the drug 32. An opening 31 may be formed in the bottom wall 25, and optionally a pierceable sterile barrier 33, such as a pierceable septum, may extend across the opening 31 to seal the interior of the housing 29 prior to use. In some embodiments, the pierceable sterile barrier 33 may be omitted, and instead a removable sealing member (not illustrated) may cover and seal close the opening 31 prior to use.

After the bottom wall 25 of the housing 29 is attached to the patient's tissue 13, the insertion mechanism 12 may be activated to move a delivery member from a retracted position within the housing 29 to a deployed position extending outside of the housing 29. In the present embodiment, this may include the insertion mechanism 12 inserting a needle or trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the needle 21, leaving the distal open end of the cannula 23 inside the patient for subcutaneous delivery of the drug 32. The needle 21 may be solid and have a sharpened end for piercing the patient's skin 11. Furthermore, the needle 21 may be made of a material that is more rigid than the cannula 23. In some embodiments, the needle 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient.

In some embodiments, the insertion mechanism 12 may include one or more springs (e.g., coil springs, torsion springs, etc.) initially retained in an energized state, and which are released upon depression of the actuator 28 in order to insert the needle 21 and cannula 23, or hollow needle, into the patient. Furthermore, retraction of the needle 21 may be achieved by the automatic release of another spring after the needle 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

The container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A from the proximal end 36 of the container 14 to a distal end 37 of the container 14 in order to expel the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A from the proximal end 36 of the container 14 to the distal end 37 of the container 14. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy. Other examples are possible.

The fluid pathway assembly 22 may be configured to establish fluid communication between the container 14 and the insertion mechanism 12 via a sterile fluid flow path during operation of the drug delivery device 10. The first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with the fluid passage 50.

The fluid pathway assembly 22 may include a first end 44 connected to the container 14, a second end 48 connected to the insertion mechanism 12, and a fluid passage 50 extending between the first end 44 and the second end 48. As described in more detail below, in some embodiments the first end 44 of the fluid pathway assembly 22 may be connected to the container 14 via a clip member 53. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29.

Figure 2:
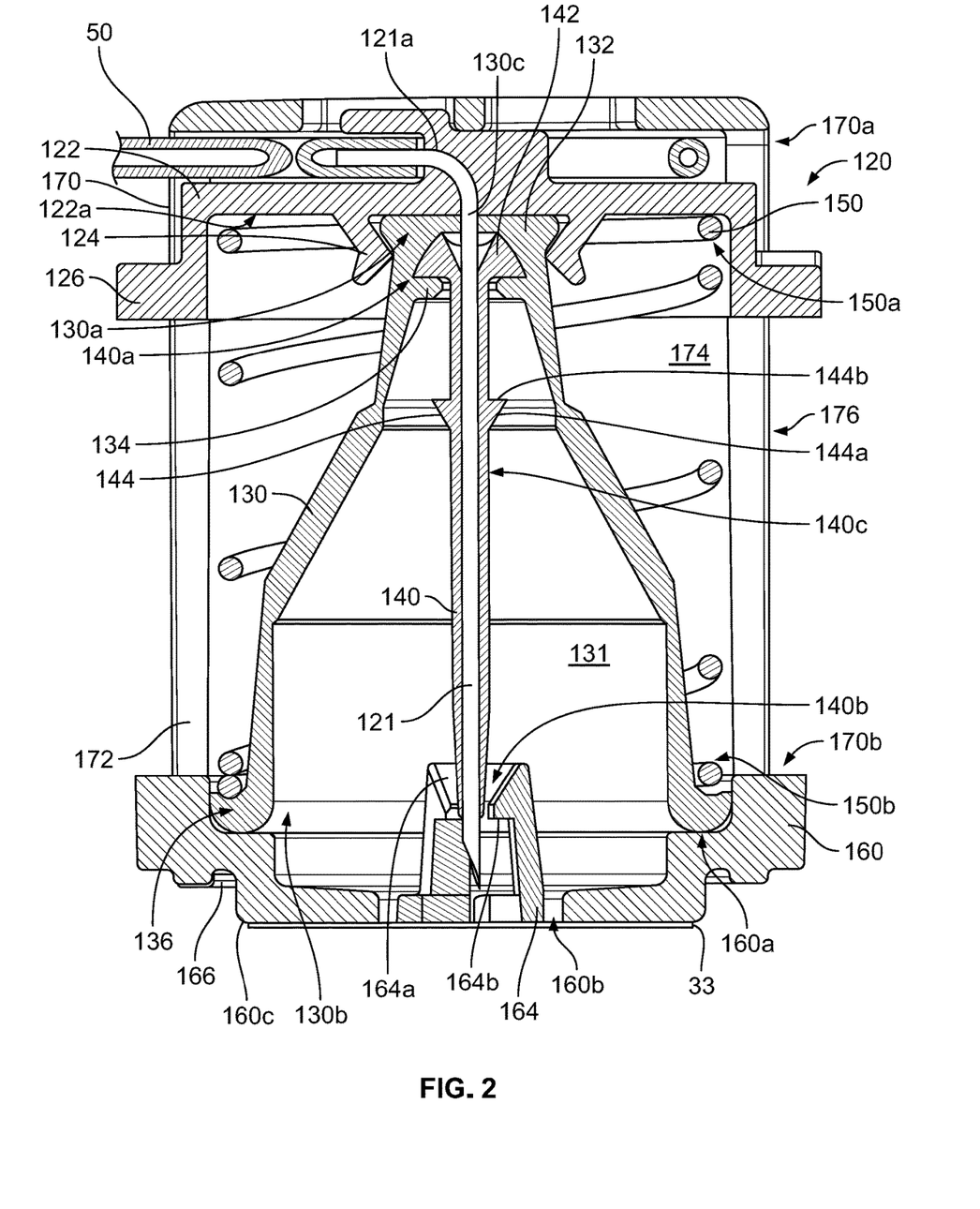
FIG. 2 illustrates a cross-sectional view of an embodiment of an insertion mechanism in a pre-fired configuration in accordance with various embodiments.
Figure 3:
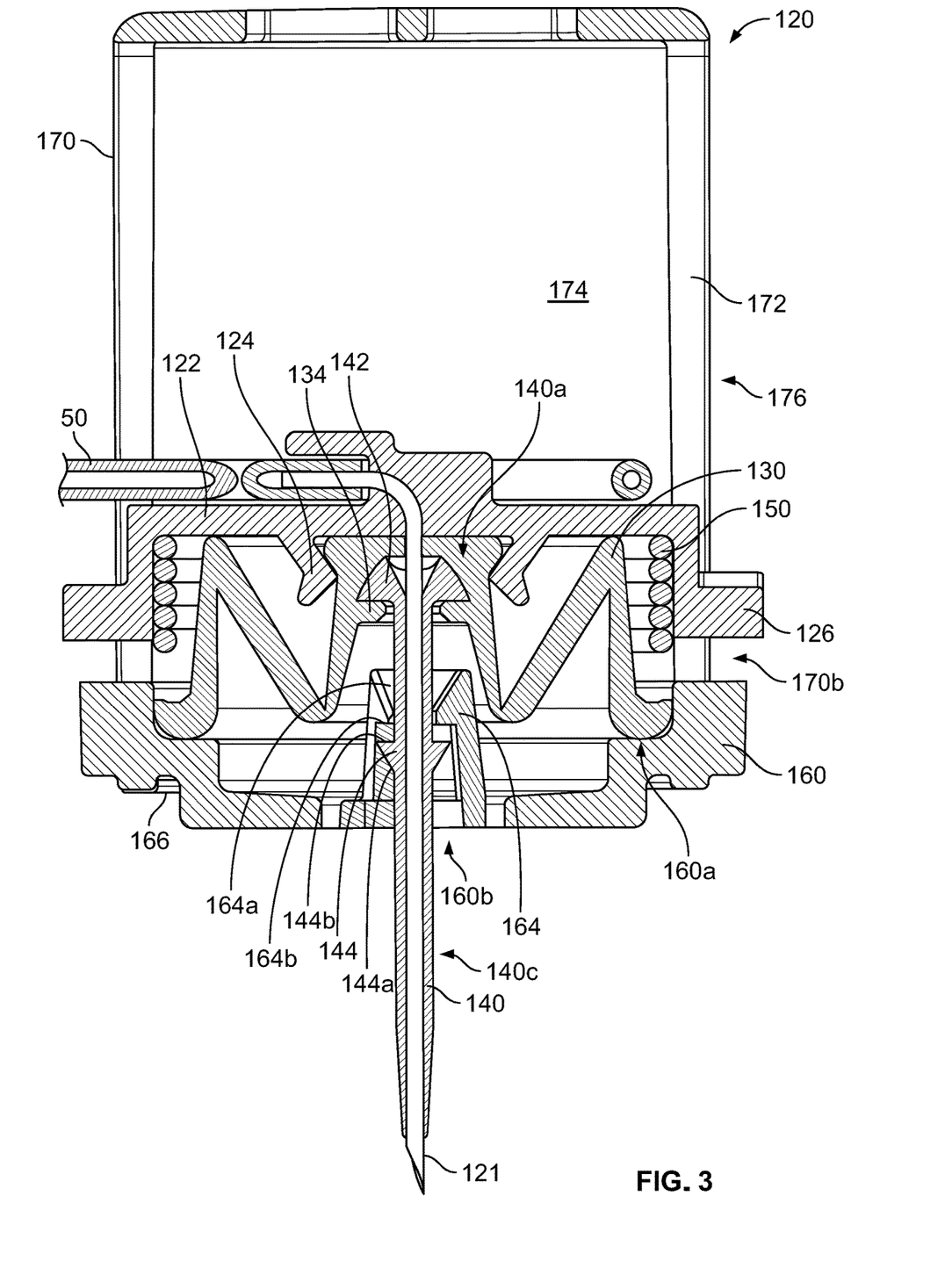
FIG. 3 illustrates a cross-sectional view of the insertion mechanism of FIG. 2 in an inserted configuration in accordance with various embodiments.
Figure 4:
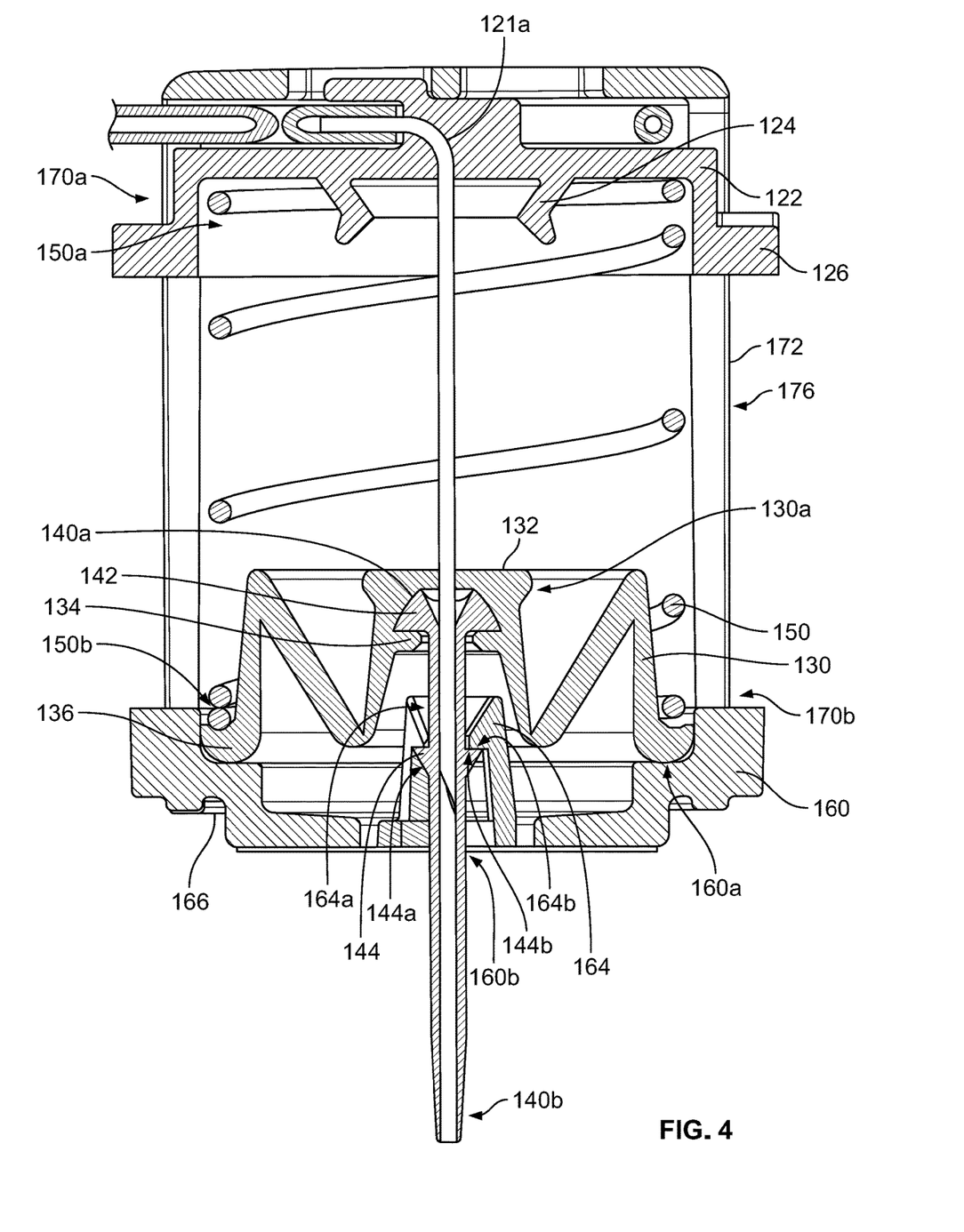
FIG. 4 illustrates a cross-sectional view of the insertion mechanism of FIGS. 2 and 3 in a retracted configuration in accordance with various embodiments.

FIGS. 2-4 illustrate one example of a needle insertion mechanism 120 corresponding to the insertion mechanism 12 illustrated in FIG. 1. The insertion mechanism 120 may be incorporated in a drug delivery device such as the drug delivery device 10 depicted in FIG. 1. The insertion mechanism 120 includes a needle hub 122, a needle or trocar 121 coupled to the needle hub 122, a flexible boot 130 being removably coupled to the needle hub 122, a cannula 140 at least partially disposed within an interior volume 131 of the flexible boot 130, an urging member 150 coupled to the needle hub 122, and a floor member 160. The needle 121 may have a hollow interior to allow for the drug 32 to flow through. The needle insertion mechanism 120 may include any number of additional components and/or features to assist in operation.

In the illustrated example, the needle hub 122 includes a lower surface 122a that includes a needle hub coupling mechanism 124 protruding therefrom. The needle hub 122 further includes any number of protrusions or tabs 126 protruding outwardly from the needle hub 122.

The flexible boot 130 has a first end 130a and a second end 130b and is removably coupled to the needle hub 122. Specifically, the first end 130a of the flexible boot 130 includes a flexible boot coupling mechanism 132 that engages the needle hub coupling mechanism 124. The first end 130a of the flexible boot 130 also includes a flexible seat or ledge 134 that protrudes inwardly into the interior volume 131 of the boot 130. In the illustrated example, the needle hub coupling mechanism 124 and the flexible boot coupling mechanism 132 are each in the form of flexible fingers, tabs, and/or or flanges whereby the flexible boot coupling mechanism 132 has a smaller outer diameter than an inner diameter of the needle hub coupling mechanism 124, and therefore, the flexible boot coupling mechanism 132 is removably insertable into the needle hub coupling mechanism 124 via a press or interference fit. In alternative examples, an outer diameter of the needle hub coupling mechanism 124 may be smaller than an inner diameter of the flexible boot coupling mechanism 132, and therefore, the needle hub coupling mechanism 124 may be removably insertable into the flexible boot coupling mechanism 132 via a press or interference fit. Other examples of couplings and/or engagements between the needle hub coupling mechanism 124 and the flexible boot coupling mechanism 132 may be used.

The flexible boot 130 may also include an opening 130c located at the first end 130a through which the needle 121 may be disposed to create a flow path from the reservoir 30 (of FIG. 1) via the fluid passage 50. In some examples, the first end 130a of the flexible boot 130 may act as a sterile barrier and/or a seal when coupled to the needle 121 whereby fluid, gas, or other contaminants cannot pass between the opening 130c of the boot 130 and the needle 121.

The cannula 140 has a first end 140a and a second end 140b, a longitudinal length 140c extending between the first end 140a and the second end 140b, and a hollow interior to accommodate the needle 121. Further, the cannula 140 has an integrated first cannula coupling mechanism 142 located near the first end 140a thereof and an integrated second cannula coupling mechanism 144 located along the longitudinal length thereof between the first and second ends 140a, 140b. In the illustrated example, the first cannula coupling mechanism 142 can be in the form of a number of tabs, outward protrusions, or an annular rib that couples the cannula 140 to the flexible boot 130 via a press or interference fit such that the cannula coupling mechanism 142 is retained by the ledge 134. In some examples, the fit between the boot 130 and the cannula coupling mechanism 142 provides a seal whereby fluid, gas, or other contaminants cannot pass between the boot 130 and the cannula 140. In other examples, other types of couplings and/or engagements between the first cannula coupling mechanism 142 and the flexible boot 130 may be used. In the illustrated example, the second cannula coupling mechanism 144 is in the form of an angled tab or annular barb that protrudes outwardly from the cannula 140.

In the illustrated example, the urging member 150 is in the form of a coil spring that includes a first end 150a and a second end 150b. The first end 150a of the urging member 150 is positioned adjacent to and in contact with the lower surface 122a of the needle hub 122. In some examples, any number of components may be disposed between the urging member 150 and the lower surface 122a of the needle hub. The second end 150b of the urging member 150b is positioned adjacent to the floor member 160. Specifically, the floor member 160 includes a facing surface 160a in the form of a ledge. The second end 130b of the flexible boot 130 includes a lip 136 that rests on the facing surface 160a. The second end 150b of the urging member 150 is positioned on top of the lip 136 of the flexible boot 130 such that the lip 136 is compressed between the urging member 150 and the facing surface 160a. So configured, the lip 136 acts as a sealing member or sterile barrier. The second end 150b of the urging member 150 may have a grounded end, meaning a lowermost surface may be generally planar to allow for uniform contact with the lip 136 to maintain a fluid tight seal between the lip 136 and the floor member 160.

The floor member 160 may also include a floor coupling mechanism 164 in the form of any number of flexible, notched fingers, angled tabs, or barbs. In the illustrated example, the floor coupling mechanism 164 is positioned around a needle port 160b in the floor member 160 and extends into the interior volume of the flexible boot 131.

The needle insertion mechanism 120 may also include an insertion mechanism housing 170 having a first end 170a and a second end 170b. The insertion mechanism housing 170 may have any shape and/or configuration (e.g., generally cylindrical in shape), and may form a shell wall 172 defining an inner volume 174. The shell wall 172 may include at least one channel 176 defined therethrough.

In the illustrated example, the needle hub 122, the needle 121, the flexible boot 130, the cannula 140, and the urging member 150 are all at least partially disposed within the inner volume 174 of the insertion mechanism housing 170. The needle hub 122, and thus the needle 121, the flexible boot 130, and the cannula 140, which are all operably coupled to the needle hub 122, are movable between the first end 170a of the insertion mechanism housing 170 and the second end 170b of the insertion mechanism housing 170. Specifically, the protrusions or tabs 126 of the needle hub 122 may be disposed in corresponding channels 176 which guide movement of the protrusions 126 between a first position at the first end 170a and a second position at the second end 170b of the insertion mechanism housing 170. The floor member 160 may be coupled to the second end 170b of the insertion mechanism housing 170 using any number of approaches to enclose, and optionally seal, the components within the inner volume 171. The floor member 160 may include the needle port 160b that corresponds to the opening 31 formed in the bottom wall of FIG. 1. Further, the pierceable sterile barrier 33 may optionally extend across the needle port 160b to seal the inner volume 174 of the shell wall 172 prior to use.

As illustrated in FIG. 2, the needle insertion mechanism 120 is in a first configuration prior to activation of the needle insertion mechanism 120. The needle hub 122 is at the first position near the first end 170a of the insertion mechanism housing 170. The urging member 150 maintains the needle hub 122 in the first position by exerting a force against the needle hub 122 (in addition to exerting a force against the lip 136 of the flexible boot 130).

Referring now to FIG. 3, the needle insertion mechanism 120 moves to a second configuration upon actuation of the drug delivery device 10. A drive mechanism (not shown) such as a spring, for example, can be initially retained in an energized state and urges the needle hub 122, and thus the needle 121, the flexible boot 130, and the cannula 140, which are all operably coupled to the needle hub 122, to the second end 170b of the insertion mechanism housing 170. The needle 121 pierces the patient's skin and the cannula 140 is inserted into the patient.

Because the needle hub coupling mechanism 124 is coupled to the flexible boot coupling mechanism 132, the flexible boot 130 bends and compresses to fit in the reduced inner volume between the needle hub 122 and the floor member 160. Similarly, because the first cannula coupling mechanism 142 is coupled to the flexible boot 130 (and additionally may be frictionally engaged by the needle 121), the cannula 140 extends through the needle port 160b of the floor member 160. As illustrated in FIG. 3, the urging member 150 moves to a compressed state in this second configuration.

In the second configuration, the second cannula coupling mechanism 144 slides to a position beyond the floor coupling mechanism 164. One or both of the second cannula coupling mechanism 144 and the floor coupling mechanism 164 may be temporarily deformed to accommodate passage of the second cannula coupling mechanism 144 past the floor coupling mechanism 164. For example, the floor coupling mechanism 164 may be deformed or deflected in an outwardly radial direction, and additionally or alternatively, the second cannula coupling mechanism 144 may be deformed in an inwardly radial direction. In the illustrated example, the second cannula coupling mechanism 144 and the floor coupling mechanism 164 both include angled surfaces 144a, 164a, respectively, that assist the second cannula coupling mechanism 144 in sliding by the floor coupling mechanism 164.

Referring now to FIG. 4, the needle insertion mechanism 120 moves to a third configuration in which the needle 121 is retracted from the patient but the cannula 140 remains in place. Specifically, the urging member 150 exerts a force on the needle hub 122 to cause it to move back to the first position at the first end 170a of the insertion mechanism housing 170. The needle 121, which is rigidly or fixedly coupled to the needle hub 122, moves with the needle hub 122 to a retracted configuration. Engagement between the second cannula coupling mechanism 144 and the floor coupling mechanism 164 prevent or restrict the cannula 140, and thus the flexible boot 130, from moving back to the first position along with the needle hub 122. Specifically, a facing surface or mating region 144b of the second cannula coupling mechanism 144 engages and abuts a corresponding facing surface or mating region 164b of the floor coupling mechanism 164 to restrict the cannula 140 from moving to the first position. As the needle hub 122 moves back to the first position, the flexible boot coupling mechanism 132 disengages from the needle hub coupling mechanism 124 while the first cannula coupling mechanism 142 remains retained by the ledge 134 of the flexible boot 130. As such, the cannula 140 remains positioned in the patient's skin while the flexible boot 130 remains at the second compressed configuration. In this configuration, the drug 32 may be dispensed to the patient by flowing through the fluid passage 50, through the needle 121, and ultimately out the second end 140b of the cannula 140.

So configured, the needle insertion mechanism 120 requires minimal components to operate while still maintaining a sealed, sterile environment. The flow path may be generally linear in configuration and have minimal bends, turns, and/or coils. As such, minimal amounts of drug may be retained in the flow path after the drug delivery process is complete.

Additionally, with respect to FIG. 2, the needle insertion mechanism 120 may be efficiently manufactured. First, a contact surface 160c of the floor member 160 may be placed on a holding surface (not shown). The floor member 160 may optionally include a locking mechanism 166 which may be used as a restraint to hold the floor member 160 and the assembled needle insertion mechanism 120 during assembly and/or sterilization. Then, the boot 130 is positioned such that the lip or contact surface 136 is disposed against the contact surface 160a of the floor member 160. At this point, the cannula 140 may already reside in connection with the boot 130, or the cannula 140 is attached to the boot 130 prior to positioning the boot 130 onto the floor member 160. To attach the cannula 140 to the boot 130, the first cannula attachment mechanism 142 is simply forced into the first end 130a of the boot 130 such that the ledge 134 of the flexible boot 130 engages the first cannula coupling mechanism 142.

Then, the urging member 150 may be disposed over and against the flexible boot 130 to retain the lip 136 between the urging member 150 and the floor member 160. The needle hub 122, with needle 121 attached, is then coupled to the flexible boot 130 and cannula 140 by inserting the needle 121 into the cannula 140 via the opening 130c at the first end 130a of the boot 130. The insertion mechanism housing 170 is finally disposed over the assembled components and against the floor member 160 such that the flexible boot 130, the urging member 150, the needle hub 122, the needle 121, and the cannula 140 are at least partially disposed in the inner volume 174.

The above description describes various systems and methods for use with a drug delivery device. It should be clear that the system, drug delivery device or methods can further comprise use of a drug or medicament listed below with the caveat that the following list should neither be considered to be all inclusive nor limiting. The medicament will be contained in a container that is either filled or pre-filled for treatment with the medicament. The container can be a cartridge or a pre-filled syringe.

For example, the drug delivery device or more specifically the container of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Epo-ratio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1 (N); L1 (N) WT; L1 (N) 1K WT; 2xL1 (N); 2xL1 (N) WT; Con4 (N), Con4 (N) 1K WT, 2xCon4 (N) 1K; L1C; L1C 1K; 2xL1C; Con4C; Con4C1K; 2xCon4C1K; Con4-L1 (N); Con4-L1C; TN-12-9 (N); C17 (N); TN8-8 (N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a);

Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5(31 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ3 mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, actuation mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

The legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. An insertion mechanism for a wearable drug delivery device, the insertion mechanism comprising:
   a needle hub being movable between a first position and a second position;
   a needle coupled to the needle hub;
   a flexible boot having a first end and a second end, the flexible boot defining an interior volume and being removably coupled to the needle hub and movable therewith between the first position and the second position;
   a cannula at least partially disposed within the interior volume of the flexible boot, the cannula having a first end, a second end, a longitudinal length extending therebetween, and a hollow interior to accommodate the needle, the cannula further having a first cannula coupling mechanism located near the first end of the cannula and a second cannula coupling mechanism located between the first and second ends of the cannula, the first cannula coupling mechanism coupled to the boot to be movable therewith between the first position and the second position;
   an urging member in contact with the needle hub to urge the needle hub towards the first position; and
   a floor member positioned near the second end of the flexible boot, the floor member having a floor coupling mechanism that extends into the interior volume of the flexible boot,
   wherein upon the needle hub occupying the second position, the second cannula coupling mechanism engages the floor coupling mechanism, thereby restricting movement of the cannula towards the first position.

2. The insertion mechanism of claim 1, wherein the floor coupling mechanism comprises a first angled tab having a first mating region, and wherein the second cannula coupling mechanism comprises a second angled tab protruding radially from the cannula and having a second mating region, wherein upon the second cannula coupling mechanism engaging the floor coupling mechanism, the first mating region of the first angled tab abuts the second mating region of the second angled tab.

3. The insertion mechanism of claim 1, wherein upon the needle hub being urged from the second position to the first position, the flexible boot disengages from the needle hub to remain at the second position.

4. The insertion mechanism of claim 1, wherein the flexible boot is removably coupled to the needle hub via an interference fit.

5. The insertion mechanism of claim 1, wherein a portion of the urging member abuts against the flexible boot to urge the flexible boot against the floor member.

6. The insertion mechanism of claim 1, wherein the urging member comprises a coil spring having a grounded end abutting against the flexible boot to form a seal against the floor member.

7. The insertion mechanism of claim 1, further comprising an insertion mechanism housing having a first end corresponding to the first position of the needle hub and a second end corresponding to the second position of the needle hub, the insertion mechanism housing defining an interior volume to accommodate the needle hub, the flexible boot, the cannula, and the urging member.

8. The insertion mechanism of claim 7, wherein the needle hub includes at least one tab, and wherein the insertion mechanism housing includes at least one channel extending between the first end and the second end thereof to accommodate and guide movement of the needle hub tab between the first position and the second position.

9. The insertion mechanism of claim 1, wherein the needle moves with the needle hub upon the needle hub being urged to the first end of the insertion mechanism housing.

10. The insertion mechanism of claim 1, wherein the floor member includes a locking mechanism to accommodate a manufacturing restraint during assembly.

11. A wearable drug delivery device comprising:
   a main housing;
   a container disposed in the main housing;
   an insertion mechanism disposed in the main housing;
   a fluid pathway connector defining a sterile fluid flow path between the container and the insertion mechanism;
   the insertion mechanism comprising:
      a needle hub being movable between a first position and a second position,
      a needle coupled to the needle hub,
      a flexible boot having a first end and a second end, the flexible boot defining an interior volume and being removably coupled to the needle hub and movable therewith between the first position and the second position,
      a cannula at least partially disposed within the interior volume of the flexible boot, the cannula having a first end, a second end, a longitudinal length extending therebetween, and a hollow interior to accommodate the needle, the cannula further having a first cannula coupling mechanism located near the first end of the cannula and a second cannula coupling mechanism located between the first and second ends of the cannula, the first cannula coupling mechanism adapted to couple the cannula to the boot to be movable therewith between the first position and the second position,
      an urging member in contact with the needle hub to urge the needle hub towards the first position, and
      a floor member positioned near the second end of the flexible boot, the floor member having a floor coupling mechanism that extends into the interior volume of the flexible boot;
      wherein upon the needle hub occupying the second position, the second cannula coupling mechanism engages the floor coupling mechanism, thereby restricting axial movement of the cannula towards the first position.

12. The wearable drug delivery device of claim 11, wherein the floor coupling mechanism comprises a first angled tab having a first mating region, and wherein the second cannula coupling mechanism comprises a second angled tab protruding radially from the cannula and having a second mating region, wherein upon the second cannula coupling mechanism engaging the floor coupling mechanism, the first mating region of the first angled tab abuts the second mating region of the second angled tab.

13. The wearable drug delivery device of claim 11, wherein upon the needle hub being urged from the second position to the first position, the flexible boot disengages from the needle hub to remain at the second position.

14. The wearable drug delivery device of claim 11, wherein the flexible boot is removably coupled to the needle hub via an interference fit.

15. The wearable drug delivery device of claim 11, wherein a portion of the urging member abuts against the flexible boot to urge the flexible boot against the floor member.

16. The wearable drug delivery device of claim 11, wherein the urging member comprises a coil spring having a grounded end abutting against the flexible boot to form a seal against the floor member.

17. The wearable drug delivery device of claim 11, further comprising an insertion mechanism housing having a first end corresponding to the first position of the needle hub and a second end corresponding to the second position of the needle hub, the insertion mechanism housing defining an interior volume to accommodate the needle hub, the flexible boot, the cannula, and the urging member.

18. The wearable drug delivery device of claim 17, wherein the needle hub includes at least one tab, and wherein the insertion mechanism housing includes at least one channel extending between the first end and the second end thereof to accommodate and guide movement of the needle hub between the first position and the second position.

19. The wearable drug delivery device of claim 11, wherein the needle moves with the needle hub upon the needle hub being urged to the first end of the insertion mechanism housing.

20. A method of manufacturing a needle injection mechanism for a wearable drug delivery device, the method comprising:

providing a floor member having a contact surface and a floor coupling mechanism extending from the contact surface;

disposing a contact surface of a flexible boot against the contact surface of the floor member, the flexible boot defining an interior volume;

disposing an urging member against the flexible boot to retain the flexible boot between the urging member and the floor member;

disposing an insertion assembly within the interior volume of the flexible boot;

coupling a needle hub to the flexible boot and the insertion assembly; and disposing a housing against the floor member such that an interior volume of the housing receives at least part of the flexible boot, the urging member, the insertion assembly, and the needle hub.

21. The method of claim 20, wherein disposing the insertion assembly in the interior volume of the flexible boot comprises:

inserting a needle through a portion of the flexible boot such that a longitudinal length of the needle is within the interior volume of the flexible boot.

22. The method of claim 20, further comprising attaching a cannula to the flexible boot prior to disposing the insertion assembly in the interior volume of the flexible boot.

23. The method of claim 20, wherein disposing the urging member against the flexible boot comprises disposing a grounded end of a coil spring against the flexible boot to form a seal.

24. The method of claim 20, wherein coupling the needle hub to the flexible boot comprises press fitting a portion of the flexible boot into an engagement region of the needle hub.

25. The method of claim 20, wherein coupling the needle hub to the needle comprises fixing a needle elbow portion of the needle to the needle hub.

* * * * *

UNITED STATES PATENT AND TRADEMARK OFFICE
CERTIFICATE OF CORRECTION

PATENT NO. : 11,103,636 B2
APPLICATION NO. : 16/015568
DATED : August 31, 2021
INVENTOR(S) : Jerome Olivas et al.

It is certified that error appears in the above-identified patent and that said Letters Patent is hereby corrected as shown below:

In the Specification

At Column 3, Line 21, "such" should be -- such as --.

At Column 8, Line 31, "and/or or" should be -- and/or --.

At Column 9, Line 18, "150b" should be -- 150 --.

At Column 11, Line 65, "Neorecormon®" should be -- NeoRecormon® --.

At Column 13, Line 8, "hu-MetG-CSF)," should be -- hu-Met-G-CSF), --.

At Column 14, Lines 23-24, "Con4C1K; 2xCon4C1K;" should be -- Con4C 1K; 2xCon4C 1K; --.

At Column 14, Line 33, "Ab1A1; Ab1F; Ab1K, Ab1P; and Ab1P," should be -- AblA1; AblF; AblK; and AblP; --.

At Column 15, Line 19, "A" should be -- 1A --.

At Column 15, Line 63, "(y4)," should be -- (γ4), --.

At Column 15, Line 66, "(K)," should be -- (κ), --.

At Column 16, Line 42, "IL-15specific" should be -- IL-15 specific --.

At Column 18, Line 43, "(nesiritide;" should be -- (nesiritide); --.

At Column 18, Line 60, "hu-MetG-CSF);" should be -- hu-Met-G-CSF); --.

At Column 18, Lines 63-64, "1Ib/IIia" should be -- IIb/IIIa --.

Signed and Sealed this
Twenty-eighth Day of June, 2022

Katherine Kelly Vidal
*Director of the United States Patent and Trademark Office*

CERTIFICATE OF CORRECTION (continued)
U.S. Pat. No. 11,103,636 B2

At Column 19, Line 11, "anti-IL-2Ra mAb);" should be -- anti-IL-2Rα mAb); --.

At Column 19, Lines 19-20, "anti-α5(31" should be -- anti-α5β1 --.

At Column 19, Line 21, "mAb" should be -- mAb); --.

At Column 19, Line 29, "anti-eotaxinl" should be -- anti-eotaxin-1 --.

At Column 19, Line 43, "anti-TGFβ3" should be -- anti-TGFß --.

At Column 20, Line 15, "cells or" should be -- cells --.